Figure 1:
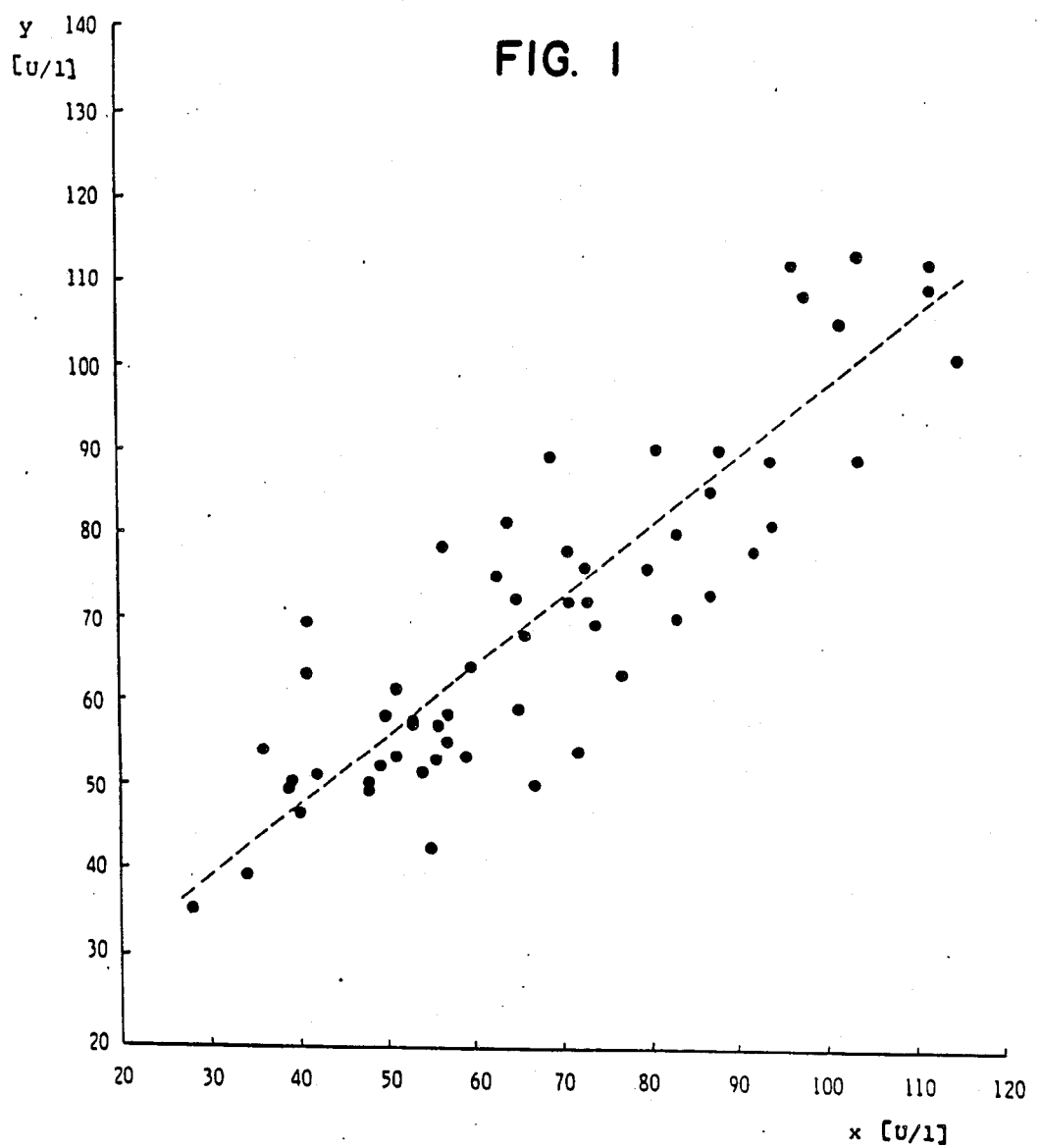

United States Patent [19]

Rosalki

[11] Patent Number: 4,681,842

[45] Date of Patent: Jul. 21, 1987

[54] PROCESS AND REAGENT FOR THE DIFFERENTIATED DETERMINATION OF ISOENZYMES OF ALKALINE PHOSPHATASE

[75] Inventor: Sidney B. Rosalki, London, United Kingdom

[73] Assignee: Boehringer Mannheim GmbH, Mannheim, Fed. Rep. of Germany

[21] Appl. No.: 653,237

[22] PCT Filed: Jan. 7, 1984

[86] PCT No.: PCT/EP84/00004

§ 371 Date: Sep. 11, 1984

§ 102(e) Date: Sep. 11, 1984

[87] PCT Pub. No.: WO84/02720

PCT Pub. Date: Jul. 19, 1984

[30] Foreign Application Priority Data

Jan. 12, 1983 [GB] United Kingdom ............... 8300685
May 23, 1983 [GB] United Kingdom ............... 8314185

[51] Int. Cl.[4] ................. C12Q 1/42; C12N 9/16

[52] U.S. Cl. ..................... 435/21; 435/196; 435/800; 435/814; 435/815; 436/827

[58] Field of Search .......... 435/21, 196, 814, 815, 435/800; 436/827, 825, 174

[56] References Cited

PUBLICATIONS

Biochimica et Biophysica Acta, 616 (1980) 41–59 Lehmann, F. G.

*Primary Examiner*—Christine M. Nucker
*Assistant Examiner*—Louanne C. Krawczewicz
*Attorney, Agent, or Firm*—Felfe & Lynch

[57] ABSTRACT

The subject of the application is a process and a reagent for the differentiated determination of the bone and liver isoenzyme of alkaline phosphatase in a sample, whereby this is mixed with a lectin which is able to bind N-acetylglucosamine residues and is incubated. Thereafter, there is carried out a separation of the lectin-bound from the free isoenzyme portions and the alkaline phosphatase activity is determined in one or in both of the separated media.

9 Claims, 4 Drawing Figures

PROCESS AND REAGENT FOR THE DIFFERENTIATED DETERMINATION OF ISOENZYMES OF ALKALINE PHOSPHATASE

Alkaline phosphatase (orthophosphoric monoester phosphohydrolase) catalyses the hydrolysis of phosphoric acid monoesters at alkaline pH values. This enzyme occurs in many tissues. There exist tissue-specific forms (isoenzymes) for example in the liver, in bones, in the small intestine, in the kidneys and in the placenta. From these organs, the isoenzymes are transmitted to the blood plasma. The characteristic properties of the particular isoenzymes are retained in the case of transfer from the producing organ into the blood plasma.

The blood plasma of healthy humans mainly contains the liver and bone isoenzymes. In the case of about one guarter of all persons, alkaline phosphatase is also found in the plasma which originates in the small intestine. In these cases, the proportion of this mall intestine isoenzyme lies at an average value of 10% of the total alkaline phosphatase content in the plasma. During pregnancy, especially during the last 3 months, alkaline phosphatase originating in the placenta is also transmitted to the blood plasma. The total alkaline phosphatase activity of the plasma is given by the sum of the activities of all tissue-specific individual components.

The determination in the plasma of the total activity of alkaline phosphatase, as well as especially of the activity of the liver and bone isoenzymes, is of especial diagnostic importance in the case of the investigation of diseases of the liver and of the bone system. The diseases bring about an increase of the alkaline phosphatase activity in the plasma since, under these conditions, alkaline phosphatase is transmitted from the liver or the bones to an increased extent. Consequently, the increase of the alkaline phosphatase activity of the liver or of the bone isoenzyme in the plasma can serve for the recognition of a disease of these tissues. In the case of a disease of the liver, in addition there arises a further enzyme variant of the alkaline phosphatase which results by complex formation of the liver isoenzyme with lipids or proteins and which is believed to be formed in the biliary tract. This so-called bile isoenzyme, which is also called high molecular, rapid or $\alpha_1$-alkaline phosphatase, can, in this case, appear in the plasma as an alkaline phosphatase component in a smaller proportion.

The differentiation of the alkaline phosphatase isoenzymes from small intestine, placenta, kidneys and bile from one another or also from the liver and the bone isoenzymes is readily possible since these tissue-specific forms clearly differ in their chemical, physical and immunological properties. Processes for the separation and determination of these isoenzymes are known and depend, for example, on the differing behaviour of the isoenzymes with regard to inhibitors, on differences in the electric charge, etc. Thus, for example, the differences in the electrophoretic mobility in alkaline buffer systems can be used for the separation of these isoenzymes.

However, only small differences are to be observed between the liver and the bone enzyme. In particular, the liver and the bone isoenzyme of the alkaline phosphatase differ only slightly with regard to the electric charge, the heat stability and in the response to inhibitors (for example with regard to urea). These differences do not suffice in order to achieve a usable differentiation between these two enzyme forms and a sufficient quantification of each form in a mixture of both forms.

It was the object of the invention to make available a new process with the help of which a differentiation and differentiated determination of the liver and bone isoenzme of alkaline phosphatase is made possible. This object is solved by the process according to the invention in which the sample, for example blood plasma or serum, is mixed with a lectin which is able to bind N-acetylglucosamine residues and incubated. Thereafter, there is carried out a separation of the lectin-bound from the free isoenzyme portions and the alkaline phosphatase activity is determined in one or in both separated media.

Lectins are carbohydrate-binding proteins. As lectins, there are especially suitable for the process according to the invention lectins from wheat germ (*Triticum vulgaris*) or from potatoes (*Solanum tuberosum*). Especially preferred is the wheat germ lectin, which is commercially available as lyophilised powder (Sigma London Chemical CO.). Lectin is preferably added to the sample in the form of a solution, preferably in water. The concentration of such lectin solutions preferably amounts to 0.1–1% (wt./vol.). Such lectins bind the bone isoenzyme more quickly than the liver isoenzyme. Due to the binding of the lectin, the physical, chemical and also immunological properties of the isoenzyme are changed so that a separation of the lectin-bound from the free isoenzyme portions is possible with the help of suitable, usual methods for this purpose.

After the addition of the lectin solution to the serum or plasma sample, the mixture is incubated. The incubation time usually amounts to 10 to 60, preferably 20 to 40 minutes. During the incubation, the temperature is kept constant, namely, in a range at which the enzyme activity is not influenced. The incubation is preferably carried out at 20° to 45° C.

Thereafter, the alkaline phosphatase activity bound to lectin is separated from the non-bound. The separation can take place, for example, with the help of electrophoresis. For this purpose, a plasma or serum sample is mixed with an equivalent amount of a lectin solution, left to stand for some time and thereafter subjected to an electrophoretic separation. Because of its binding to the lectin, the bone enzyme does not migrate in the case of the electrophoresis, whereas the liver enzyme is not impaired in its electroporetic behaviour. Consequently, whereas in samples not treated with lectin, the two isoenzymes do not display ascertainable differences in their speed of migration, after the lectin treatment, because of the migration speed differences, one can clearly differentiate between the two isoenzyme forms.

The separated zones can be coloured and determined in known manner, for example by densitometric measurement of the electrophoresis membrane.

The electrophoretic separation is preferably carried out with the help of cellulose acetate membranes. However, there can also be used membranes of other materials, for example of agarose, agar gel or of a polyacrylamide gel.

The electrophoretic separation between the bone and liver isoenzyme can be further improved when the lectin is contained in a buffer solution. As buffer, tris-barbital buffer has proved to be especially suitable. The concentration of the lectin in the buffer solution preferably amounts to 1 to 10% (wt./vol.). According to this embodimental form of the process according to the invention, the electrophoresis membrane is first impregnated with the lectin-containing buffer solution and then mixed with the sample solution and incubated. The electrophoresis is carried out with the same buffer solution but without lectin addition. There is obtained a clear separation of the bone and liver isoenzyme fraction.

Since the addition of lectin also brings it about that the isoenzyme bound to lectin precipitates out, a separation can also be achieved by centrifuging. If the sample contains almost exclusively bone isoenzyme, then the centrifuge supernatant displays a negligible alkaline phosphatase activity. If the serum sample mainly contains liver isoenzyme, then, due to the addition of lectin, only a relatively small proportion of the alkaline phosphatase activity precipitates out. With the help of sera with known content of bone and liver isoenzymes, reference values can be determined on the basis of which the activity of bone or liver isoenzyme can be determined in unknown samples.

With the help of the electrophoresis, it could be shown that the alkaline phosphatase activity in the supernatant originates mainly from the liver isoenzyme. With knowledge of the fact that the total amount of bone isoenzyme and only a small and relatively constant proportion of the liver isoenzyme can be removed from a mixture of both isoenzymes by the addition of lectin and subsequent centrifuging, the amount of liver isoenzyme of alkaline phosphatase in a mixture of the bone and liver isoenzyme in unknown ratios can be determined easily.

A preferred embodimental form of the process according to the invention consequently consists in that the blood or plasma sample, possibly after separation of other isoenzymes of alkaline phosphatase, is mixed with wheat germ or potato lectin, incubated and thereafter centrifuged. The supernatant is separated from the centrifugate. In the supernatant, there is determined the liver isoenzyme, whereby it is to be taken into account that a small but constant proportion of the liver isoenzyme is always coprecipitated. The taking into account expediently takes place with the help of reference values which have been obtained on the basis of samples with known content of liver isoenzymes.

For the determination of the bone isoenzyme, the centrifugate is resuspended, expediently with a salt solution, for example a solution of sodium chloride in water. The salt concentration preferably amounts to 0.5–1% (wt./vol.). Again to resuspend the precipitate has the further advantage that the small intestine isoenzyme is no longer contained in this suspension. Advantageously, so much salt solution is added that the original volume of the sample is again achieved. In the suspension so obtained, the alkaline phosphatase activity is determined in known manner. With the help of comparison samples, it can be shown that about 80% of the bone isoenzyme is present in this suspension. By comparison with reference values, which have been determined on the basis of samples with known isoenzyme content, it could be shown that by multiplication of the activity found in the suspension by the factor 1.25, there is obtained a good correlation of the values which have been found according to the process according to the invention for the bone isoenzyme with values which are obtained according to other methods.

One can obtain the activity of the liver isoenzyme with reasonable accuracy from the total activity of the alkaline phosphatase, by subtracting the value which has been found according to the present process for the bone isoenzyme.

If the sample to be measured contains bile isoenzyme, then this appears partly in the precipitate. In these cases, it is expedient to remove the bile isoenzyme before the carrying out of the process according to the invention. This can be achieved by the addition of the lectins concavalin A or ricin. These lectins selectively bind the bile isoenzyme without displaying a binding effect on the liver or bone isoenzyme.

To the salt solution which is used for the resuspension of the precipitate, there is expediently added a solubilising material, for example sodium dodecyl sulphate. Such an addition is not connected with an inhibition of the lectin-bound isoenzyme. The concentration of the solubilising material in the solution amounts to 5–20 g./l., preferably 8–12 g./l.

Furthermore, it is possible to separate the free isoenzyme from the lectin-bound isoenzyme portion in that one adds a solution of N-acetylglucosamine and separates the mixture obtained electrophoretically. The concentration of N-acetylglucosamine amounts to 1–50, preferably to 5–20 g./l.

The separation between the two isoenzymes can, in principle, also take place according to other known methods, for example on the basis of differentiated binding effects towards ion exchangers, with the help of gel chromatography or with the help of isoelectric focusing. All these separation methods depend upon the fact that, by the combination of the isoenzyme with the lectin, the chemical, physical and immunological behaviour is changed, for example, change of the electric charge relationships, or change of the mole mass, etc.

The lectins usable according to the invention, for example wheat germ lectin, do not bind the small intestine isoenzyme in any noteworthy amount. However, they bind the bile isoenzyme very strongly. However, the small intestine and bile isoenzyme are very easily differentiatable from one another and from the bone and liver isoenzyme and are quantifiable, for example by electrophoresis, chromatography or on the basis of their reaction with inhibitors. From the total activity and fron the activity of the small intestine and bile isoenzyme, which can be separately determined, if they are present, and from the knowledge of the differing effects of a lectin usable according to the invention on the bone and liver isoenzyme, the activity of each individual one of these tissue-specific isoenzymes of the alkaline phosphatase in the blood plasma or serum can be determined individually.

A further subject of the invention is a reagent for the carrying out of a process for the differentiation of isoenzymes of alkaline phosphatase, which is characterised in that it contains a lectin which is able to bind N-acetylglucosamine residues. The reagent contains the lectin preponderantly in dissolved form, preferably in the form of an aqueous solution. The concentration of lectin preferably amounts of 0.1–1% (wt./vol.). However, the reagent can also be present in dry, preferably lyophilised form. This form is usually obtained in that the abovementioned aqueous solutions are lyophilised.

EXAMPLE 1

A sample of a serum of a patient with a bone or liver disease is mixed with the same amount of an aqueous lecithin solution which contains 5 g. of wheat germ lectin in one liter of water. A wheat germ lectin used is a lyophilised powder of Triticum vulgaris of the firm Sigma London Chemical Co. The mixture is incubated for 30 minutes at 37° C. Thereafter, a usual electrophoretic separation is carried out with the help of a cellulose acetate membrane. The alkaline phosphatase activity is determined in the separated zones by usual colouring processes or by densitometric measurement.

EXAMPLE 2

Equal volumes of an aqueous lectin solution, prepared from 5 g. wheat germ lectin of the firm Sigma Chemical Co. and one liter of water, and of the sera to be tested are mixed. Besides the bone and liver isoenzyme, the sera are to contain only negligible amounts of other isoenzymes of alkaline phosphatase. If larger, non-negligible amounts of other enzymes were present, then these are to have been separated off previously with the help of usual known processes. The mixtures of sample and lectin solution are incubated at 37° C. for 30 minutes and thereafter centrifuged. The supernatant is removed. The precipitate is resuspended in a 0.9% (wt./vol.) sodium chloride solution. The alkaline phosphatase activity in the suspension is determined. The activity found is multiplied by the factor 1.25 and gives the content of bone isoenzyme in the sample.

The total activity of alkaline phosphatase in the sample is determined in the usual way. From the difference of the total activity and of the measured value for the bone isoenzyme, the content of liver isoenzyme, in the sample can be determined.

In FIG. 1 to FIG. 4, the values for sera found according to this process for healthy humans and also for humans suffering from a bone or liver disease are compared with the values which have been determined by conventional methods of successive selective heat inactivation.

In detail, there are illustrated:

FIG. 1: Comparison of the alkaline phosphatase activity of the bone isoenzyme, determined by treatment with wheat germ lectin (y) and by selective heat inactivation (x). Temperature 30° C.; n=59 (healthy subjects); y=0.84×+14.03; r=0.89.

Figure 2:
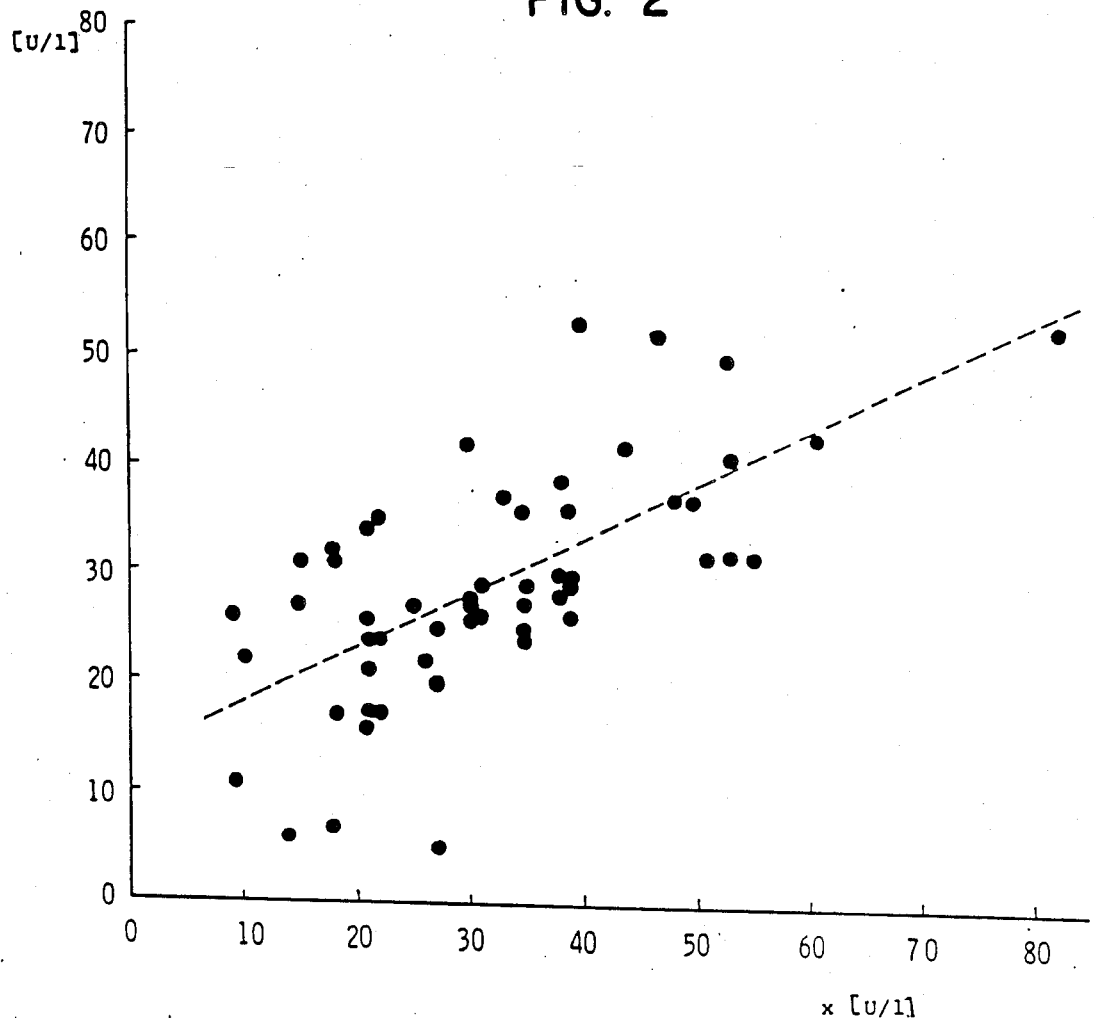

FIG. 2: Comparison of the alkaline phosphatase activity of the liver isoenzyme, determined by treatment with wheat germ lectin (y) and by selective heat inactivation (x). Temperature 30° C.; n=59 (healthy subjects); y=0.49×+13.27; r=0.66.

Figure 3:
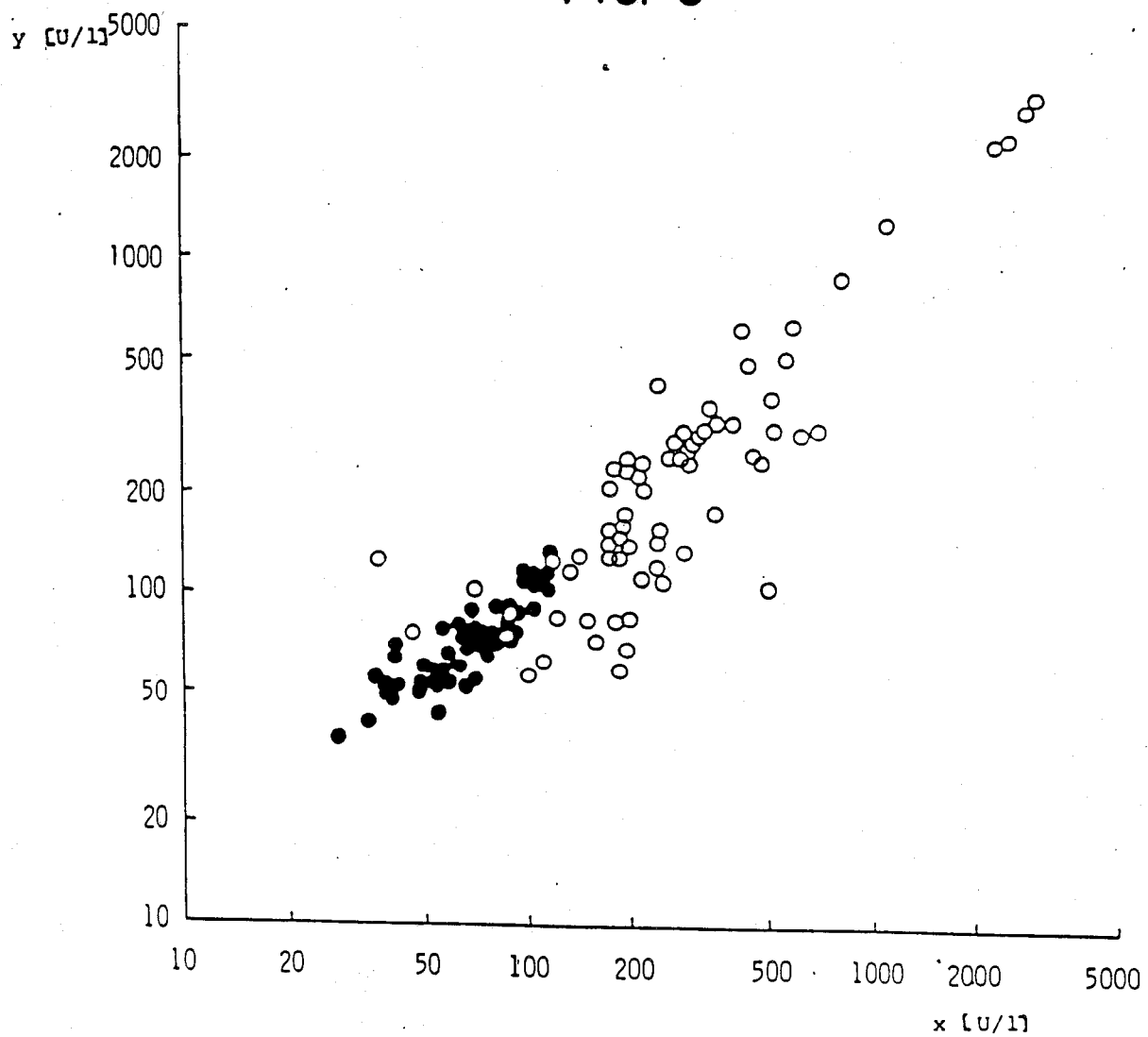

FIG. 3: Comparison of the alkaline phosphatase activity for the bone isoenzyme, determined by treatment with wheat germ lectin (y) and by selective heat inactivation (x). Temperature 30° C.; n=133 healthy subjects (●) and subjects suffering from a bone disease (○); y=0.97×−9.96; r=0.98.

Figure 4:
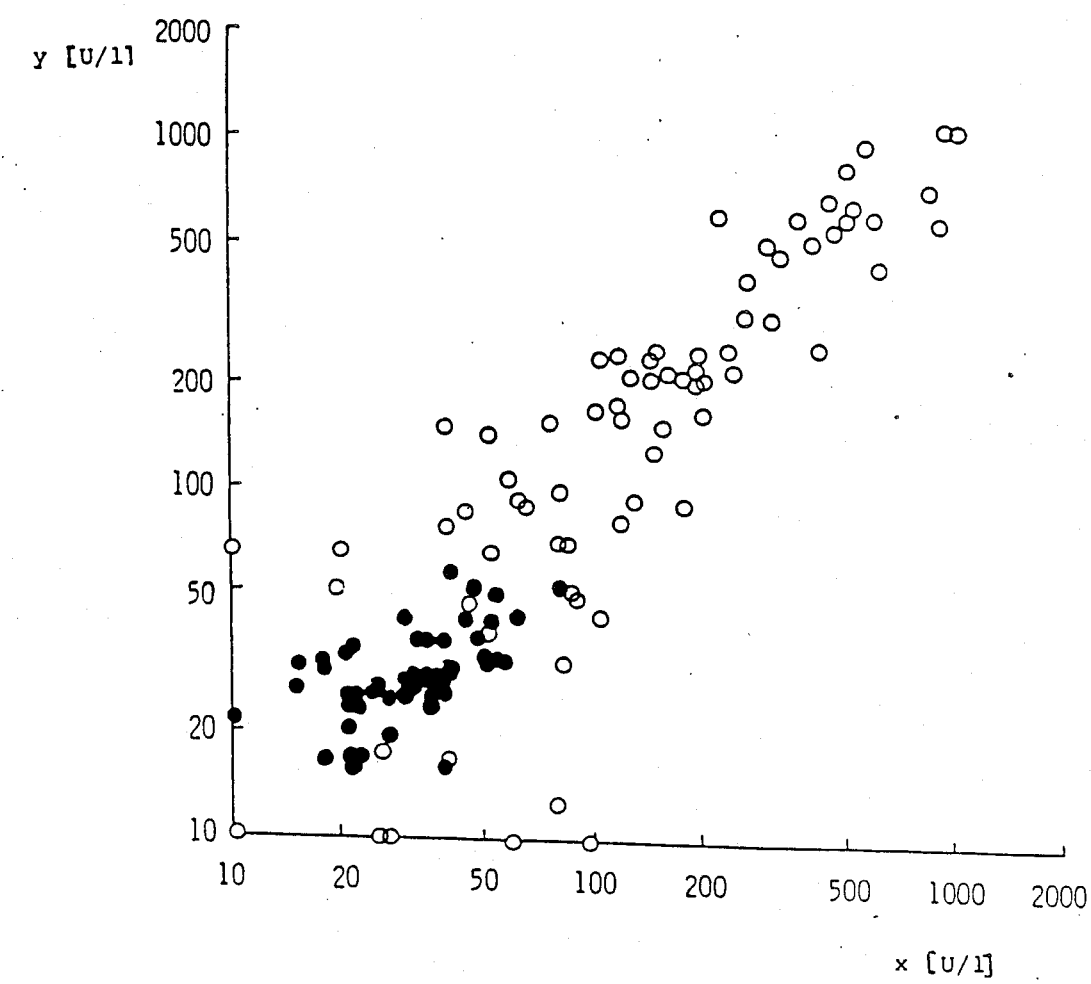

FIG. 4: Comparison of the alkaline phosphatase activity of the liver isoenzyme, determined by treatment with wheat germ lectin (y) and by selective heat inactivation (x). Temperature 30° C.; n=133 healthy subjects (●) and subjects suffering from a bone disease (○); y=1.02×+14.34; r=0.93.

I claim:

1. Process for the differentiation of bone and liver isoenzymes of alkaline phosphatase in a sample containing both enzymes comprising mixing the sample with a solublized lectin which binds N-acetylglucosamine residues of the bone isoenzyme, incubating the mixture obtained for a time sufficient to bind all bone isoenzymes to form a lectin bound portion and a free isoenzyme portion containing liver isenzyme, separating the lectin bound portion from the free isoenzyme portion and determining the alkaline phosphatase activity in one or both of the portions.

2. Process according to claim 1, wherein the lectin is wheat germ or potato lectin.

3. Process according to claim 1, wherein said lectin is in a 0.1–1% (wt/vol) aqueous solution.

4. Process according to claim 1 wherein the lectin bound portion is separated from the free isoenzyme portion by putting bound and free isoenzyme portions onto a support and adding a current so as to separate said portions.

5. Process according to claim 4, wherein the support is selected from the group consisting of cellulose acetate, agarose, agar gel, and polyacrylamide gel base membranes.

6. Process according to claim 1, wherein the lectin-bound portion is separated from the free isoenzyme portion by centrifuging, said lectin-bound portion forming a precipitate.

7. Process according to claim 6, when, after the centrifuging, the precipitate is resuspended in a salt solution.

8. Process according to claim 7, wherein said salt solution is a 0.5–1% (wt/vol.) sodium chloride solution.

9. Process according to claim 7, wherein a solubilizing material is added to the salt solution.

* * * * *